United States Patent [19]
Sieben et al.

[11] Patent Number: 6,033,916
[45] Date of Patent: *Mar. 7, 2000

[54] MEASURING DEVICE AND METHOD FOR MAKING SAME

[75] Inventors: Ulrich Sieben, Reute; Bernhard Wolf, Stegen; Hellmut Haberland, Bötzingen; Christoph Cremer, Heidelberg, all of Germany

[73] Assignee: Micronas Intermetall GmbH, Freiburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/785,630

[22] Filed: Jan. 17, 1997

[30] Foreign Application Priority Data

Jan. 17, 1996 [DE] Germany .......................... 196 01 488

[51] Int. Cl.⁷ ................................................ G01N 33/543
[52] U.S. Cl. .................. 436/518; 156/625.1; 156/643.1; 422/55; 422/57; 422/82.01; 422/82.05; 427/2.13; 427/496; 427/551; 427/569; 427/576; 427/578; 427/579; 427/421; 435/4; 436/524; 436/525
[58] Field of Search .......................... 422/55, 57, 82.01, 422/82.05, 82.11; 427/2.13, 496, 551, 569, 576, 578, 579, 421; 156/625.1, 643.1; 435/4; 436/518, 524, 525

[56] References Cited

U.S. PATENT DOCUMENTS

| | | |
|---|---|---|
| 3,926,564 | 12/1975 | Giaever .................................. 428/336 |
| 4,090,849 | 5/1978 | Healey et al. ........................... 156/664 |
| 4,334,880 | 6/1982 | Malmros . |
| 4,777,019 | 10/1988 | Dandekar . |
| 4,820,649 | 4/1989 | Kawaguchi et al. ..................... 436/501 |
| 5,124,172 | 6/1992 | Burrell et al. ........................... 436/525 |
| 5,418,136 | 5/1995 | Miller et al. ................................. 435/5 |
| 5,496,701 | 3/1996 | Pollard-Knight ..................... 422/82.11 |

FOREIGN PATENT DOCUMENTS

| | | |
|---|---|---|
| 29 47 050 A1 | 5/1981 | Germany . |
| 195 12 117 A1 | 10/1996 | Germany . |
| WO 88/09499 | 12/1988 | WIPO . |

OTHER PUBLICATIONS

N. Jaffrezic–Renault and C. Martelet, "Preparation of well–engineered thin molecular layers on semiconductor–based transducers" Sensors and Actuators—A Physical A 32, (1992), pp. 307–312.

Primary Examiner—Christopher L. Chin
Attorney, Agent, or Firm—Akin, Gump, Strauss, Hauer & Feld, L.L.P.

[57] ABSTRACT

A measuring device for measuring or examining physiological parameters on biocomponents includes an FET sensor 5 whose electrical protective layer 12 is roughened or has a structured coating 15. The structuring of the active sensor contact surface 12 is adapted to the outer contour and topography of the biocomponent in question, so that a better possibility is available for anchoring the biocomponents to the contact surface 24 forming the FET protective layer of the sensor 5.

7 Claims, 2 Drawing Sheets

MEASURING DEVICE AND METHOD FOR MAKING SAME

BACKGROUND OF THE INVENTION

The invention pertains to a process for producing a device for measuring or investigating physiological parameters in biological components ("biocomponents"). The device has at least one sensor having a measuring structure with an active contact surface for the biological components. In addition, the invention relates to a measuring device produced according to the process.

Biosensors continue to gain in importance with the very large number of cellular microsystems. The combination of a biological microsystem with a physical transducer permits the conversion of primary signal responses of the biological system into an electrical signal, which can then be registered and processed further without difficulty. Common to all sensors is that the primary sensory function of the system is assumed by a living cell or its components (e.g., receptors, gamma-globulins), and that their output signals are received by different, physical transducers.

It has become apparent in the development and testing of sensors that not all cell types or biocomponents can produce equally good contact with the transducer surfaces. To be sure, in many cases obtaining good adhesion for batch processes has succeeded through the choice of culture conditions. Nonetheless, the conditions for flow injection batches cannot be guaranteed for all cells or the like. In particular, such cells from animal cell lines which did not originally come from tumor cells are problematic in this respect. Furthermore, there is the difficulty with immune sensors on an FET basis that an optimal immobilization of the antibodies used requires an alignment of the reactive epitopes in order to receive a better signal response.

BRIEF SUMMARY OF THE INVENTION

The object of the present invention is to increase the mechanical anchoring of biocomponents (e.g., cells, receptors, gamma globulins) on the active contact surfaces of the sensors and further to improve the signal transmission properties and measurement sensitivity further.

For accomplishing this objective in accordance with the invention, it is proposed that the active contact surface of the sensor be structured approximately corresponding to the outer contours of the biocomponent in question. Through this structuring of the active contact surface, the biocomponents (e.g., cells, biological molecules, parts of cells and the like), which themselves manifest topographies having structuring effects in the nanometer range, can be anchored essentially more stably on the contact surface so that, among other things, a good long-term stability exists, and the sensor can be maintained operative for a longer period of time with living cells or the like. It is at the same time especially advantageous if the shape of the biocomponents is preferably incorporated by means of a replica technique, and if the contact surface coating is provided with a complementary reverse structuring corresponding approximately to the shape of the biocomponents especially by means of a plasma bombarding technique or etching technique.

A direct adaptation of the surface structure or profiling to the topography of the biological systems or the biocomponents to be deposited consequently takes place, by means of which an especially good anchoring is assured. The transfer of the topography of the biocomponents to the active contact surface can take place with a known replica technique.

A modified form of the process provides that material particles for cluster formation, preferably comprising about 12,000 atoms with a kinetic energy smaller than about 1 eV/atom, are bombarded or sputtered onto the active contact surface for the formation of a contact surface coating with a loose structure or gaps.

An anchoring layer can thereby be built up on the contact surface of the sensor so that it which has a comparatively loose, porous structure. Gaps or holes are thereby formed in which, for example, immune receptors can be anchored. These biocomponents are very well anchored by interlocking, and the sensors thereby manifest a much better long term stability. At the same time, one also obtains an essentially greater measurement sensitivity, as the distance between the biocomponents and sensor contact surface is at least diminished, and the charge transfer process, which influences the sensor, consequently transpires closer to the sensor.

The measuring device produced according to the process of the invention is characterized in that the active contact surface of the sensors has a surface topography approximately adapted to the shape of the biocomponent to be examined. In this connection, it is particularly appropriate if the surface topography of the sensor contact surface is basically a complementary reverse structuring of the biocomponent in question. The advantages already presented in connection with the sensor production process are manifest thereby.

It is advantageous if the sensor has a field effect transistor with a contact surface coating, preferably of aluminum oxide, silicon nitride or similar structuring material. In comparison to the contact surface of silicon oxide, which is very smooth, aluminum oxide or silicon nitride has the advantage that roughened surfaces fitting the structure of the biocomponents can also be created with them. Aluminum oxide has a high pH sensitivity and a high sensitivity toward physiological signals, and improves the electrical coupling of a cell or similar biocomponent to the field effect transistor and consequently increases its output signal. Silicon nitride has a high voltage sensitivity.

BRIEF DESCRIPTION OF THE SEVERAL VIEWS OF THE DRAWING

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
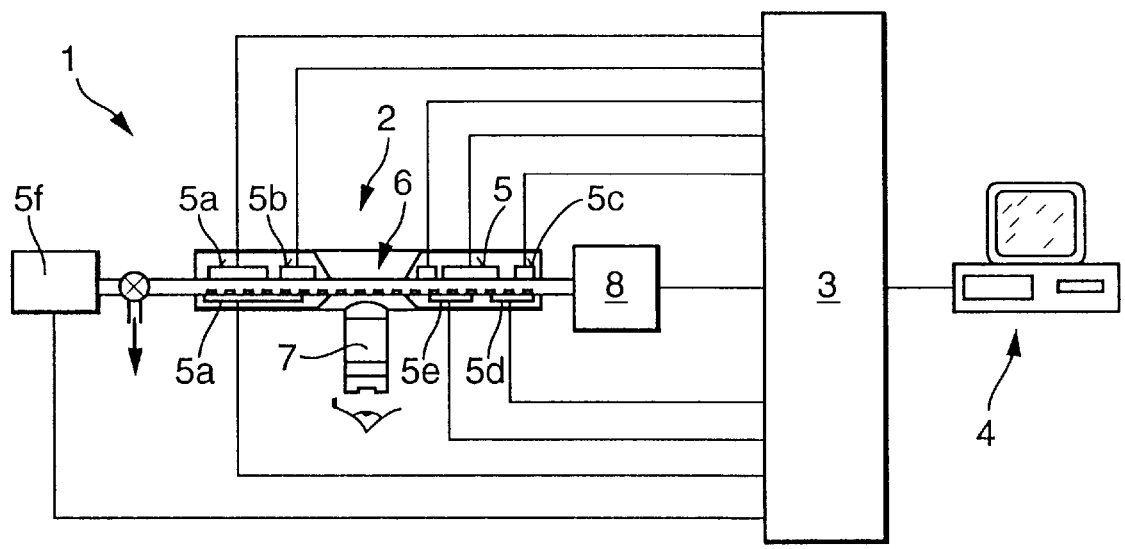
FIG. 1 is a schematic representation of a biomedical sensor system with various sensors.

A biomedical sensor system 1 depicted in FIG. 1 has a miniaturized chamber 2 for accommodation of cells to be examined, whose function is to be investigated by various discrete sensors 5. These sensors are connected with a sensor activation and signal preprocessing facility 3, which for its part is connected with a computer 4 for gathering measurement data and for evaluation, as well as for controlling the course of measurement and temperature regulation.

In the embodiment epicted, optical sensors 5*a*, an oxygen sensor 5*b*, temperature sensors 5*c*, as well as cell potential measurement sensors 5*d*, interdigital structures 5*e* for impedance measurements, and if needed, external sensors 5*f* are also used in addition to sensors 5 with a field effect transistor structure. A microscope 7 is also indicated in connection with the area of observation 6 of the sensor system 1. Designated by 8 is a function block for medium, test substances, pumps and the like. This function block as well as the sensors are connected with the sensor control and signal preprocessing facility 3. The microsensors have the most varied geometies but are always so constructed, such that either living cells are situated in their immediate vicinity, and/or the cells are an integral component part of the microsensor.

Figure 2:
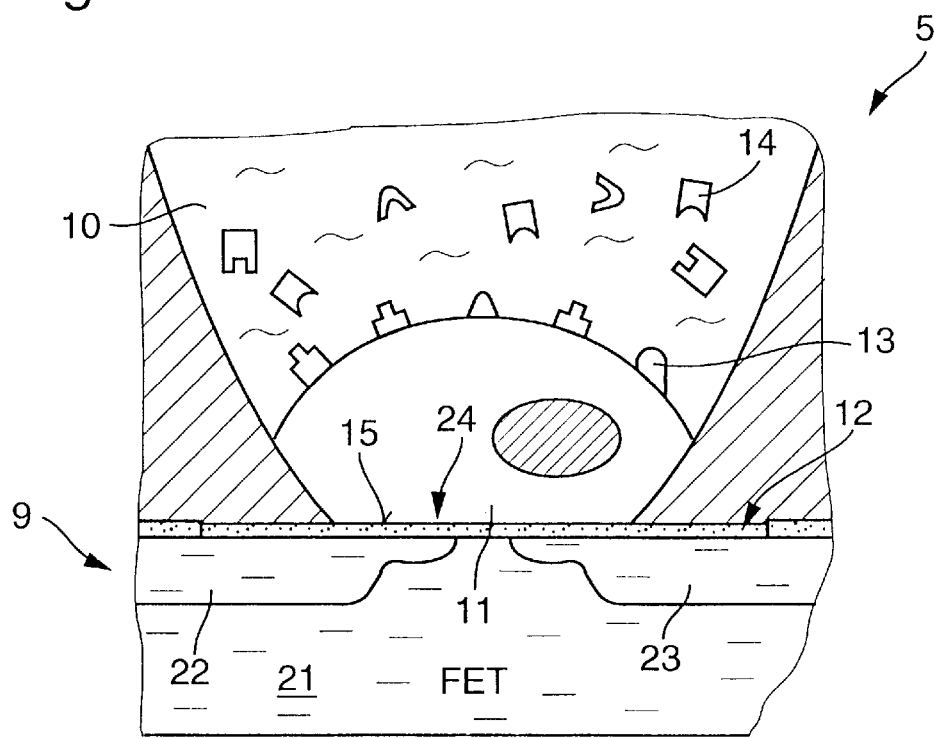
FIG. 2 is a schematic representation of an FET sensor.

FIG. 2 shows an individual FET sensor 5 which has a field effect transistor 9 which reacts very sensitively to electric fields. This field effect transistor 9 has a silicon substrate 21 into which highly doped zones 22, 23 for drain and source are diffused with the conduction type opposed to the substrate. Above that, a silicon oxide layer 12 is situated as a dielectric which forms an active sensor contact layer on the exterior, by which the FET can be controlled.

A drop of nutrient solution 10 with the cells 11 contained in it is situated on the silicon oxide layer 12. Every cell 11 carries different receptors 13 on its membrane. Suitable messenger substances 14, which can anchor themselves on the cells by the respective receptors adapted thereto, swim to the receptors in the nutrient solution 10. This leads to induced changes in molecular bonds and shifts in electric charges. The thus induced change in electric parameters is detected by the field effect transistor 9 and converted into an electric signal. An electrical transmission thereby arises from a biological signal transmission. This can then be amplified without difficulty and electrically read out and processed further for diagnostic purposes.

Since the silicon oxide layer 12, which serves as an active contact surface 24 of the sensor 5, is only slightly structured, not all cells adhere to this silicon oxide layer for a long time. It is therefore provided that the active contact surface 24 of the FET sensor is structured and thereby adapted to the exterior cell structure. The cells themselves are comparitively sharply structured and have many indentations and bulges. The external structuring of the active contact surface 24 is depicted greatly enlarged in FIG. 3 for clarification. The coating 15 of the active contact surface of the sensor 5 is recognizable here. It consists here of deposited aluminum oxide clusters 16, which are indicated by round circles. An intensive beam can be produced in a vacuum from such clusters. If one bombards or sputters these against a surface, a different structure results according to the energy of the beam. With low energies (0.1 eV per atom), rough, porous coatings with hollow spaces emerge. The roughness and structure of the surface can be varied by the kinetic energy of the cluster. From about 10 eV/atom, very smooth layers are obtained. At about 1 eV/atom, suitable roughnesses in the nanometer range emerge.

The clusters form a composite whose structure depends, among other things, upon the energy with which it is applied to the dielectric layer 12 of the field effect transistor 9. As already mentioned above, experiments have shown that roughness suitable for anchoring cells results when the kinetic energy of the bombarding cluster amounts to approximately 1 eV/atom. About 5000 atoms are thereby deposited in a cluster in any given case, whereby each cluster has a diameter of about 10 nanometers. The possibility exists, however, of depositing larger aluminum oxide clusters with about 12,000 atoms per cluster and lower kinetic energy on the FET layer 12.

Figure 3:
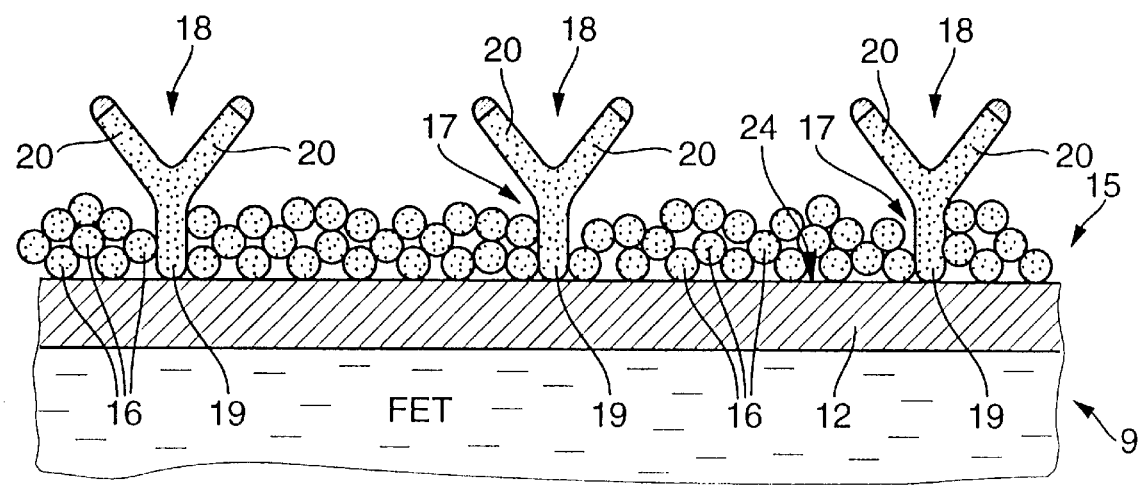
FIG. 3 is a schematic representation of an FET sensor with coating and deposited immune receptors.

The deposited clusters 16 are then oxidized and tempered, which leads to a porous but hard aluminum oxide layer. The aluminum oxide layer can be processed by various techniques (e.g., plasma bombardment technique, etching), so that cracks and gaps 17 arise. As indicated in FIG. 3, immune receptors 18 (e.g., gamma-globulin, a Y-shaped biological molecule) can, for example, be particularly well directly anchored in the holes thus arising, which can have a diameter of about 10 nm. Since now the charge transfer process, which influences the FET transpires much closer to the FET, because the intermediate function of the cell itself is switched off, an essentially higher electrical signal is to be expected. The measurement sensitivity is thereby correspondingly improved.

Silicon nitride, among others, can be used instead of aluminum oxide as a structuring material. The structuring material used in any given case is guided by the relevant requirements for the measuring procedure in question. Thus, silicon nitride is used when an increased voltage sensitivity is needed, while aluminum oxide is used when the requirements for pH sensitivity are great.

The immune receptors 18 are formed by Y-shaped biological molecules., which engage directly into the porous, ceramic structure with their support region 19, with which they normally stick in the cell wall, whereby they are very well anchored and whereby the sensors generally have a much better long term stability. The two sensorially sensitive ends 20 of the immune receptors 18 protrude outwardly from the coating 15. The anchoring of the immune receptors 18 in the coating 15 can take place by a sedimentation process with subsequent rinsing stages.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for producing a measuring device for measuring or examining physiological parameters of biological components, comprising providing at least one sensor having a measuring structure with an active contact surface for receiving the biological components, and structuring the active contact surface of the sensor to correspond approximately to outer contours of biological components to be measured or examined, wherein the active contact surface has at least one of gaps and holes capable of anchoring the biological components.

2. The process according to claim 1, wherein the step of structuring the active contact surface comprises depositing onto the surface by bombardment or sputtering material particles for cluster formation to form a cluster coating, and subsequently oxidizing and tempering the cluster coating.

3. The process according to claim 2, wherein the material particles comprise aluminum oxide.

4. The process according to claim 2, wherein the material particles comprise about 5000 atoms each and are applied to the active contact surface with a kinetic energy of about 1 eV/atom.

5. The process according to claim 1, wherein a shape of the biological components is taken up by means of a replica technique and wherein the step of structuring comprises a complementary reverse structuring.

6. The process according to claim 5, wherein the replica technique is selected from the group consisting of plasma bombardment and etching.

7. The process according to claim 2, wherein the material particles comprise about 12,000 atoms and are applied to the surface with a kinetic energy of less than about 1 eV/atom to form a contact surface coating (15) with a comparatively loose structure.

* * * * *